United States Patent
Reustle et al.

(10) Patent No.: US 11,806,148 B2
(45) Date of Patent: Nov. 7, 2023

(54) CONTROLLING OPTICAL POWER IN A SENSOR WITH THE USE OF A FARADAY CAGE

(71) Applicant: COVIDIEN LP, Mansfield, MA (US)

(72) Inventors: Linden A. Reustle, Milliken, CO (US); Sarah L. Hayman, Boulder, CO (US); Jacob Dove, Lafayette, CO (US); Shai Fleischer, Modi In (IL); Derek L. Moody, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 309 days.

(21) Appl. No.: 16/785,728

(22) Filed: Feb. 10, 2020

(65) Prior Publication Data

US 2021/0244303 A1    Aug. 12, 2021

(51) Int. Cl.
*A61B 5/24* (2021.01)
*A61B 5/00* (2006.01)

(52) U.S. Cl.
CPC .............. *A61B 5/24* (2021.01); *A61B 5/742* (2013.01); *A61B 2562/182* (2013.01)

(58) Field of Classification Search
CPC ..... A61B 5/24; A61B 5/742; A61B 2562/182; A61B 5/02427
See application file for complete search history.

(56) References Cited

U.S. PATENT DOCUMENTS

| 5,469,845 A | 11/1995 | Delonzor et al. |
| 7,796,403 B2 | 9/2010 | Coakley |
| 2002/0165440 A1* | 11/2002 | Mason ............... H05K 1/189 29/846 |
| 2008/0117616 A1 | 5/2008 | Coakley |
| 2008/0197301 A1* | 8/2008 | Diab ............... A61B 5/6826 250/505.1 |
| 2014/0228659 A1 | 8/2014 | Besko |
| 2015/0157269 A1 | 6/2015 | Lisogurski et al. |

OTHER PUBLICATIONS

International Application No. PCT/US2021/017194 International Search Report and Written Opinion dated May 3, 2021, 11 pages.

* cited by examiner

*Primary Examiner* — Amanda K Hulbert
*Assistant Examiner* — Philip C Edwards
(74) *Attorney, Agent, or Firm* — Fletcher Yoder, P.C.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor also includes a faraday cage disposed around the detector, wherein the faraday cage includes an aperture configured to limit an amount of light from the LED that the detector is able to detect.

16 Claims, 5 Drawing Sheets

CONTROLLING OPTICAL POWER IN A SENSOR WITH THE USE OF A FARADAY CAGE

FIELD

The present disclosure relates generally to medical devices, and more particularly, to medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

As technologies advance and more measurements become available from the attenuated light signals, many caregivers find it convenient to have multiple physiological measurement parameters available in a single, multi-parameter monitoring device.

SUMMARY

The techniques of this disclosure generally relate to medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting diode (LED) communicatively coupled to the communication interface and a detector, communicatively coupled to the communication interface, capable of detecting light. The patient monitoring sensor further includes a faraday cage disposed around the detector, wherein the faraday cage includes an aperture configured to limit an amount of light from the LED that the detector is able to detect.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, communicatively coupled to the communication interface, capable of detecting light. The patient monitoring sensor further includes a faraday cage disposed around the detector, wherein the faraday cage includes an aperture configured to limit an amount of light from the LED that the detector is able to detect.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Advances in light-emitting diode (LED) technology have led to LEDs that are much brighter than previously available LEDs. When these brighter LEDs are used in currently available patient monitoring sensors, the detectors of the patient monitoring sensors can become saturated. Some currently available patient monitoring sensors attempt to address this problem by using electronic circuits to control a drive current supplied to the LED and to thereby limit the amount of light emitted by the LED. In addition to the complexity of adding a drive circuit to the patient monitoring sensors, such drive current manipulation to control the light emitted by the LED may not be feasible as LED technology continues to evolve.

The present invention relates to medical sensors and monitors, in particular to systems and methods for controlling optical power in a patient monitoring sensor with the use of a faraday cage. In exemplary embodiments, a patient monitoring sensor is provided in which a detector is disposed within a faraday cage that has an opening that is configured to limit the amount of light that reaches the detector. In addition to limiting the amount of light that can reach the detector, the faraday cage provides protection against electromagnetic interference for the detector.

Figure 1:
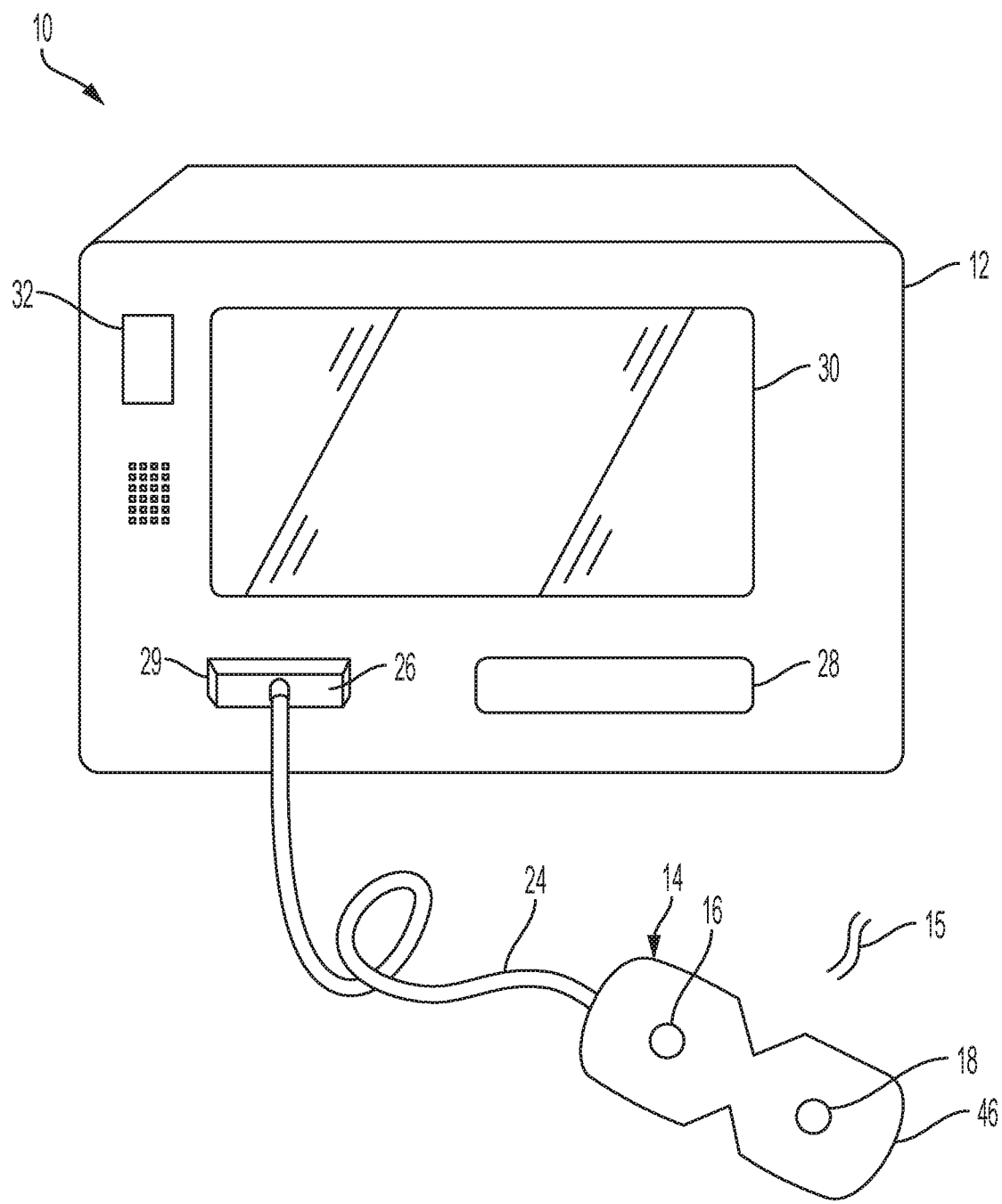
FIG. 1 illustrates a perspective view of a patient monitoring system including a patient monitor and a patient monitoring sensor, in accordance with an embodiment.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, Colo.), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal. The sensor 14 also includes a sensor body 46 to house or carry the components of the sensor 14. The sensor 14 may be reusable (such as a durable plastic clip sensor), disposable (such as a fabric adhesive sensor), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
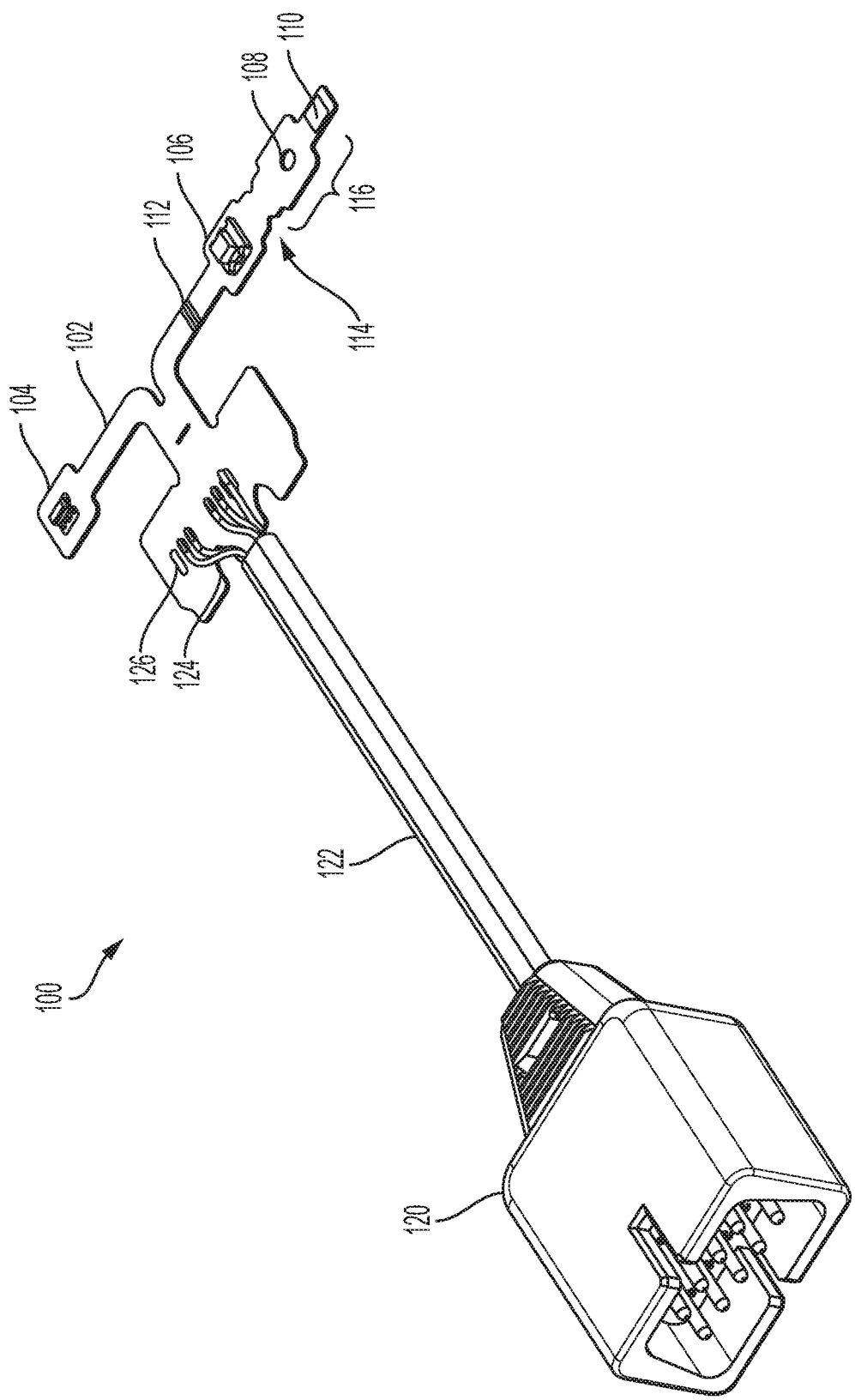
FIG. 2 illustrates a perspective view of a patient monitoring sensor, in accordance with an embodiment.

Referring now to FIG. 2, an embodiment of a patient monitoring sensor 100 in accordance with an embodiment is shown. The sensor 100 includes a body 102 that includes a flexible circuit. The sensor 100 includes an LED 104 and a detector 106 disposed on the body 102 of the sensor 100. The body 100 includes a flap portion 116 that includes an aperture 108. The flap portion 116 is configured to be folded at a hinge portion 114 such that the aperture 108 overlaps the detector 106. In one embodiment, the flap portion 116 includes an adhesive 110 that is used to secure the flap portion 116 to the body 102 after the flap portion 116 is folded at the hinge portion 114.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 108. In addition, one of the terminals 126 connect a ground wire to the flexible circuit.

In exemplary embodiments, the aperture 108 is configured to limit the amount of light that is received by the detector 106. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to control the amount of light that is received by the detector 106. In one embodiment, the aperture 108 is configured such that approximately eighty percent (80%) of a sensor portion of the detector 106 is unobstructed and able to receive light from the LED 104. In another embodiment, the aperture 108 is configured such that approximately sixty percent (60%) of a sensor portion of the detector 106 is unobstructed and able to receive light from the LED 104. In one embodiment, the aperture 108 includes a single round opening having a diameter of 0.062 inches or about 1.6 mm In another embodiment, the aperture 108 includes a plurality of openings that have a combined area of about 2 mm$^2$. In one embodiment, the active area of the photodetector is about 1.6 mm×1.6 mm, or 2.66 mm$^2$.

In exemplary embodiments, the body 102 includes a visual indicator 112 that is used to assure proper alignment of the flap portion 116 when folded at the hinge portion 114. In one embodiment, the visual indicator 112 includes two adjacent portions located such that when the end of the flap portion is placed between the two adjacent portions the aperture 108 is properly aligned over the detector 106. In another embodiment, the visual indicator 112 includes a single line that is disposed such that when the end of the flap portion is placed on top of the line the aperture 108 is properly aligned over the detector 106.

Figure 3:
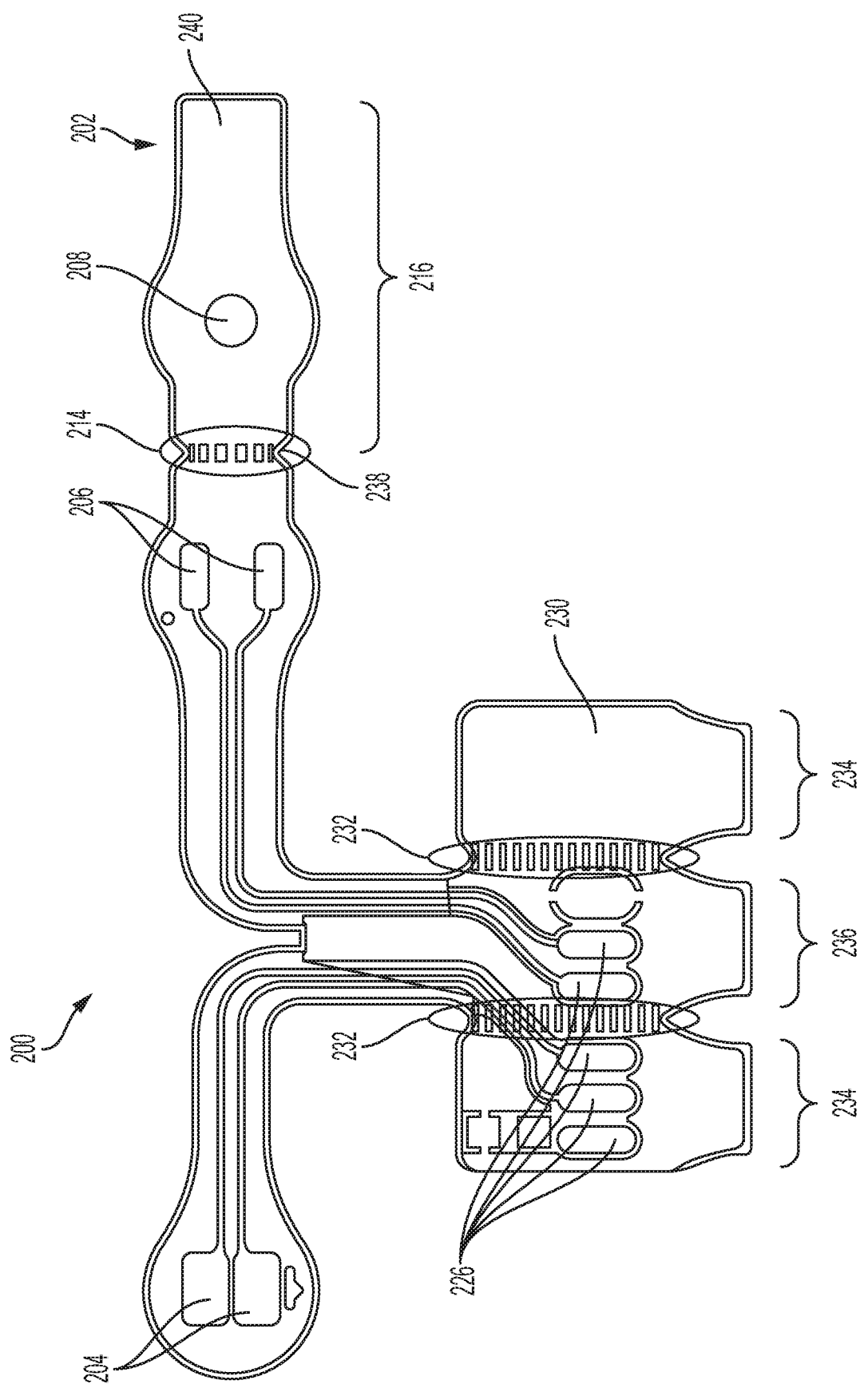
FIG. 3 illustrates a schematic view of a patient monitoring sensor, in accordance with an embodiment.

Referring now to FIG. 3, an embodiment of a patient monitoring sensor 200 in accordance with an embodiment is shown. The sensor 200 includes a flap portion 216 that is configured to be folded about a hinge portion 214 such that the aperture 208 overlaps the detector (not shown). The sensor 200 includes a flexible circuit that includes a first conductive material 230 and a second conductive material 240. The first conductive material 230 and a second conductive material 240 are both ground plane layers, but are disposed on separate physical layers and they are electrically connected through 4 vertical vias. The first conductive material 230 is configured to electrically connect the terminals 226 to contacts 204, 206 used for the LED and the detector. The second conductive material 240 is used, at least in part, to create a faraday cage around the detector, when the flap portion 216 of the sensor 202 is folded about the hinge portion 214. In one embodiment, the second conductive material 240 consists of copper. In exemplary embodiments, the hinge portion 214 includes a notch 238 which is configured to aid in the alignment of the flap portion 216 by providing a weak point for the bend to occur.

In exemplary embodiments, the hinge portion 214 includes a limited amount of the second conductive material 240 to facilitate folding the flap portion 216 while maintaining an electrical connection between the second conductive material 240 disposed in the flap portion 216 with the remaining second conductive material 240 in the sensor 200. The sensor 200 also includes hinge portions 232 which likewise include a limited amount of the first conductive material 230 to facilitate folding flap portions 234 onto a central portion 236. In exemplary embodiments, folding the flap portion 234 over top of the central portion 236 shields the detector signal as the flap portion 234 is solid ground plane copper. In addition, by folding flap portion 234 makes the sensor 200 narrower which makes it fit onto neonatal patients and fingers of adults.

Figure 4A:
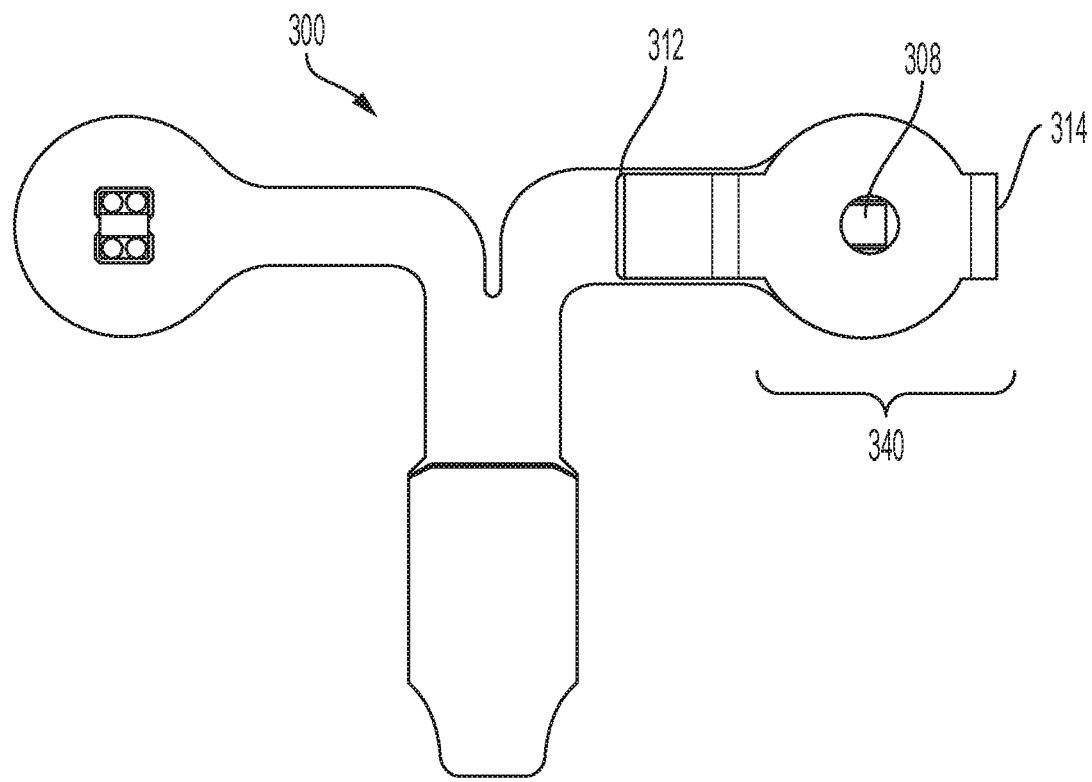
FIGS. 4A and 4B illustrate schematic views of a patient monitoring sensor, in accordance with an embodiment.
Figure 4B:
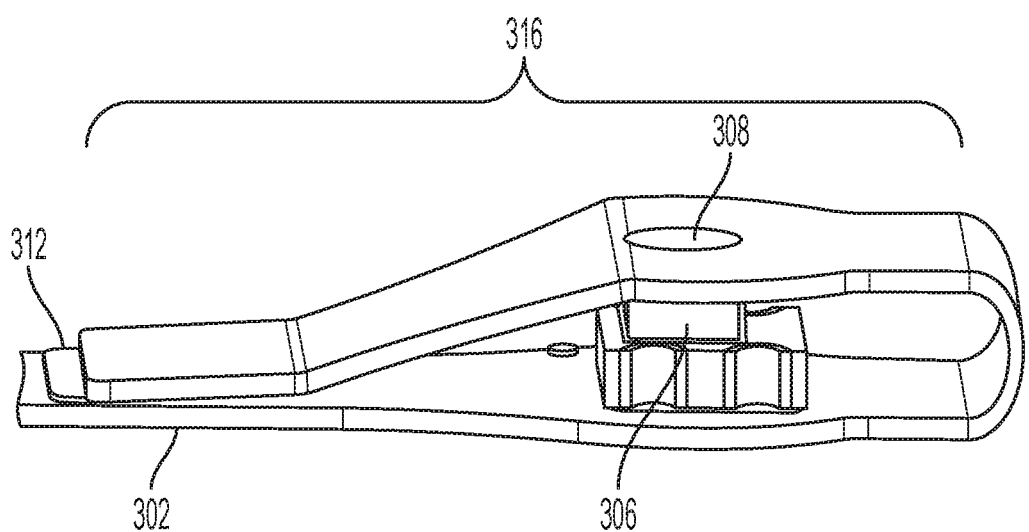

Referring now to FIGS. 4A and 4B a patient monitoring sensor 300 in accordance with an embodiment is shown. In exemplary embodiments, a faraday cage 340 is formed around the detector 306 by folding the flap portion 316 over a portion of the body 302 of the sensor 300. As illustrated, the sensor 300 includes a visual indicator 312 that is used as an alignment guide to ensure that aperture 308 is properly aligned with the detector 306, when the flap portion 316 is in the folded position.

Figure 5A:
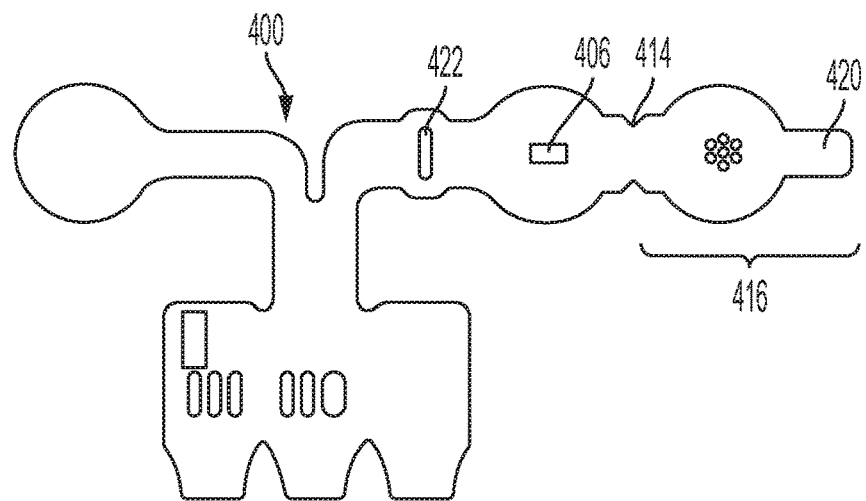
FIGS. 5A, 5B and 5C illustrate schematic views of a patient monitoring sensor, in accordance with an embodiment.
Figure 5B:
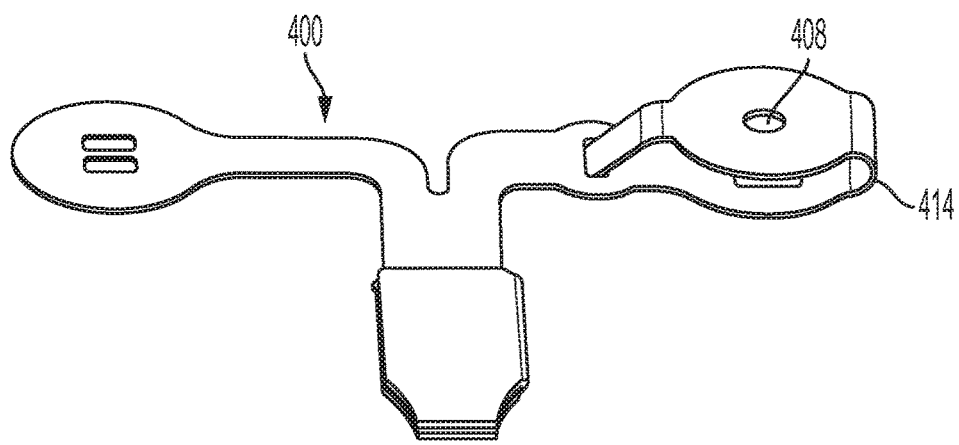
Figure 5C:
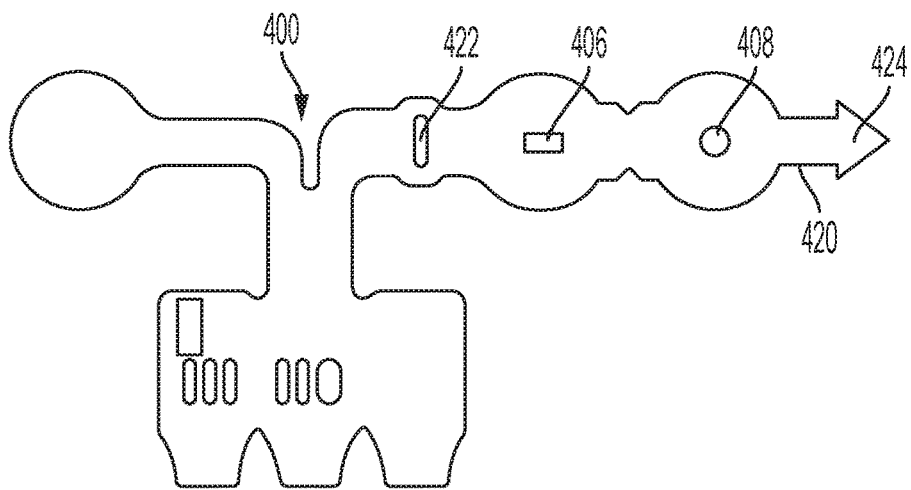

Referring now to FIGS. 5A, 5B and 5C a patient monitoring sensor 400 in accordance with an embodiment is shown. As illustrated, the flap portion 416 of the sensor 400 includes a tapered end 420 that is configured to be inserted into a slot 422 when the flap portion 416 is folded about the hinge portion 414, i.e., in the folded position. In exemplary embodiments, fully inserting the tapered end 420 into the slot 422 ensures proper alignment between the aperture 408 and the detector 406. In exemplary embodiments, the aperture 408 includes a plurality of openings in a pattern. In embodiments having multiple openings in a pattern, a larger variance in the alignment of the aperture 408 and the detector 406 is permitted. As discussed above, the configuration of the aperture 408, i.e., a number, shape, placement and size of the openings that define the aperture 408 can vary and are selected to control the amount of light that is received by the detector 406. In one embodiment, to reduce the impact of misalignment, the pattern of openings defining the aperture 408 extends beyond the dimensions of the detector 408. Accordingly, in the cases where manufacturing misalignments occur, the approximate light attenuation would stay consistent.

In one embodiment, best shown in FIG. 5C, the patient monitoring sensor 400 includes a locking member 424 disposed on the end of the tapered portion 420. The locking member 424 is configured to prevent the tapered portion 420 from becoming dislodged once the tapered portion is inserted into the slot 422. In one embodiment, the locking member 424 is configured to be temporally deformable such that it can be inserted into the slot 422. Once the locking member 424 is fully inserted into the slot, the locking member will return to its original shape and prevent the tapered portion 420 from being removed from the slot 422. In another embodiment, the locking member 424 is rotatably affixed to the tapered portion 420 and is rotated to facilitate insertion into the slot 422 and again to prevent the tapered portion 420 from being removed from the slot 422.

One or more specific embodiments of the present techniques will be described below. In an effort to provide a concise description of these embodiments, not all features of an actual implementation are described in the specification.

It should be appreciated that in the development of any such actual implementation, numerous implementation-specific decisions must be made, which may vary from one implementation to another. In an embodiment, a medical monitoring system includes a sensor that is actively powered during use.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A patient monitoring sensor, comprising:
    a communication interface, through which the patient monitoring sensor can communicate with a monitor;
    a light-emitting diode (LED) communicatively coupled to the communication interface;
    a detector, communicatively coupled to the communication interface, capable of detecting light;
    a body having a flexible circuit that couples the LED and the detector to the communication interface; and
    a faraday cage comprising a flap portion of the body extending from a portion of the body housing the detector, wherein the flap portion is configured to be folded over the detector, and wherein the flap portion defines an aperture configured to limit an amount of light from the LED that the detector is able to detect.

2. The patient monitoring sensor of claim 1, wherein the aperture includes a plurality of openings.

3. The patient monitoring sensor of claim 1, wherein the flap portion of the sensor is joined to the body of the sensor by a hinge.

4. The patient monitoring sensor a claim 3, wherein the hinge includes conductive material to electrically connect the body of the sensor to the flap portion of the sensor.

5. The patient monitoring sensor of claim 1, further comprising a visual indicator disposed on the body such that when an end of the flap portion is placed adjacent to the visual indicator, the aperture is properly aligned over the detector.

6. The patient monitoring sensor of claim 5, wherein the flap portion includes an adhesive configured to secure the end of the flap portion to the body.

7. The patient monitoring sensor of claim 1, wherein the flexible circuit includes a first conductive material, and wherein the flap portion includes a second conductive material to create the faraday cage around the detector.

8. The patient monitoring sensor of claim 7, wherein the second conductive material comprises copper.

9. A patient monitoring system, comprising:
    a patient monitor coupled to a patient monitoring sensor, the patient monitoring sensor comprising:
        a communication interface, through which the patient monitoring sensor can communicate with the patient monitor;
        a light-emitting diode (LED) communicatively coupled to the communication interface;
        a detector, communicatively coupled to the communication interface, capable of detecting light;
        a body having a flexible circuit that couples the LED and the detector to the communication interface; and
        a faraday cage comprising a flap portion of the body extending from a portion of the body housing the detector, wherein the flap portion is configured to be folded over the detector, and wherein the flap portion defines an aperture configured to limit an amount of light from the LED that the detector is able to detect.

10. The patient monitoring system of claim 9, wherein the aperture includes a plurality of openings.

11. The patient monitoring system of claim 9, wherein the flap portion of the sensor is joined to the body of the sensor by a hinge.

12. The patient monitoring system o claim 11, wherein the hinge includes conductive material to electrically connect the body of the sensor to the flap portion of the sensor.

13. The patient monitoring system of claim 11, wherein the patient monitoring sensor further comprises a visual indicator disposed on the body such that when an end of the flap portion is placed adjacent to the visual indicator, the aperture is properly aligned over the detector.

14. The patient monitoring system of claim 13, wherein the flap portion includes an adhesive configured to secure the end of the flap portion to the body.

15. The patient monitoring system of claim 9, wherein the flexible circuit includes a first conductive material, and wherein the flap portion includes a second conductive material to create the faraday cage around the detector.

16. The patient monitoring sensor of claim 15, wherein the second conductive material comprises copper.

* * * * *